«12» United States Patent
Bauss et al.

«10» Patent No.: US 7,192,938 B2
«45» Date of Patent: *Mar. 20, 2007

US007192938B2

«54» METHOD OF TREATMENT USING BISPHOSPHONIC ACID

«75» Inventors: Frieder Bauss, Neuhofen (DE); Bernhard Pichler, Ketsch (DE); Stephen Turley, Bottmingen (CH)

«73» Assignee: Hoffmann-La Roche Inc., Nutley, NJ (US)

«*» Notice: Subject to any disclaimer, the term of this patent is extended or adjusted under 35 U.S.C. 154(b) by 0 days.

This patent is subject to a terminal disclaimer.

«21» Appl. No.: 10/998,849

«22» Filed: Nov. 29, 2004

«65» Prior Publication Data

US 2005/0075319 A1    Apr. 7, 2005

Related U.S. Application Data

«63» Continuation of application No. 10/430,007, filed on May 6, 2003.

«30» Foreign Application Priority Data

May 10, 2002   (EP) ................... 02010136

«51» Int. Cl.
*A61K 31/675* (2006.01)
*A61K 31/66* (2006.01)

«52» U.S. Cl. .............. 514/89; 514/102; 514/108
«58» Field of Classification Search ............. 514/108
See application file for complete search history.

«56» References Cited

U.S. PATENT DOCUMENTS

| | | | |
|---|---|---|---|
| 3,962,432 A | 6/1976 | Schmidt-Dünker |
| 4,054,598 A | 10/1977 | Blum et al. |
| 4,267,108 A | 5/1981 | Blum et al. |
| 4,327,039 A | 4/1982 | Blum et al. |
| 4,407,761 A | 10/1983 | Blum et al. |
| 4,621,077 A | 11/1986 | Rosini et al. |
| 4,624,947 A | 11/1986 | Blum et al. |
| 4,666,895 A | 5/1987 | Bosies et al. |
| 4,705,651 A | 11/1987 | Staibano |
| 4,719,203 A | 1/1988 | Bosies et al. |
| 4,746,654 A | 5/1988 | Breliere et al. |
| 4,761,406 A | 8/1988 | Flora et al. |
| 4,777,163 A | 10/1988 | Bosies et al. |
| 4,812,311 A | 3/1989 | Uchtman |
| 4,876,248 A | 10/1989 | Breliere et al. |
| 4,922,007 A | 5/1990 | Kieczykowski et al. |
| 4,927,814 A | 5/1990 | Gall et al. |
| 4,970,335 A | 11/1990 | Isomura et al. |
| 4,971,958 A | 11/1990 | Bosies et al. |
| 5,002,937 A | 3/1991 | Bosies et al. |
| 5,018,651 A | 5/1991 | Hull et al. |
| 5,019,651 A | 5/1991 | Kieczkowski |
| 5,206,253 A | 4/1993 | Bosies et al. |
| 5,344,825 A | 9/1994 | Khanna et al. |
| 5,356,887 A | 10/1994 | Brenner |
| 5,358,941 A | 10/1994 | Bechard et al. |
| 5,431,920 A | 7/1995 | Bechard |
| 5,462,932 A | 10/1995 | Brenner et al. |
| 5,488,041 A | 1/1996 | Barbier et al. |
| 5,882,656 A | 3/1999 | Bechard et al. |
| 5,994,329 A | 11/1999 | Daifotis et al. |
| 6,124,314 A | 9/2000 | Cameron et al. |
| 6,143,326 A | 11/2000 | Mockel et al. |
| 6,294,196 B1 | 9/2001 | Gabel et al. |
| 6,419,955 B1 | 7/2002 | Rolf-Dieter et al. |
| 6,432,932 B1 | 8/2002 | Daifotis et al. |
| 6,468,559 B1 | 10/2002 | Chen et al. |
| 6,544,967 B2 | 4/2003 | Daifotis et al. |
| 6,573,252 B1 | 6/2003 | Del Soldato |
| 6,638,920 B2 | 10/2003 | Thompson |
| 6,680,307 B1 * | 1/2004 | Bauss et al. ............. 514/102 |
| 6,692,764 B2 | 2/2004 | Katdare et al. |
| 6,699,850 B2 | 3/2004 | Scolnick et al. |
| 6,770,289 B2 | 8/2004 | Uria |
| 6,838,584 B2 | 1/2005 | Blizzard et al. |
| 7,008,640 B2 | 3/2006 | Watanabe et al. |
| 2001/0051616 A1 | 12/2001 | Karpf et al. |

(Continued)

FOREIGN PATENT DOCUMENTS

CA    2308532    12/2000

(Continued)

OTHER PUBLICATIONS

Merck & Co., NJ, USA, Merck Index 13th, 2001, No. 4899.

(Continued)

*Primary Examiner*—Raymond J. Henley, III
«74» *Attorney, Agent, or Firm*—George W. Johnston; Patricia S. Rocha-Tramaloni; David E. Wildman

«57» ABSTRACT

The present invention refers to a pharmaceutical composition of a bisphosphonic acid or salt thereof, and an excipient thereof, and a method of treating disorder characterized by pathologically increased bone resorption comprising orally administering at least 150% of the expected efficious daily dose of a bisphosphonic acid or a pharmaceutically acceptable salt thereof and one or more pharmaceutically acceptable excipients thereof and administering the dose at a period of one two or three consecutive days per month.

30 Claims, No Drawings

U.S. PATENT DOCUMENTS

| | | |
|---|---|---|
| 2002/0006441 A1 | 1/2002 | Rolf-Dieter et al. |
| 2003/0118634 A1 | 6/2003 | Schofield et al. |
| 2003/0139378 A1 | 7/2003 | Daifotis et al. |
| 2003/0175340 A1 | 9/2003 | McCallister et al. |
| 2003/0195171 A1 | 10/2003 | Daifotis et al. |
| 2003/0225039 A1 | 12/2003 | Bauss et al. |
| 2004/0087550 A1 | 5/2004 | Zanetti et al. |
| 2004/0097469 A1 | 5/2004 | Little et al. |
| 2004/0147484 A1 | 7/2004 | Boyd et al. |
| 2005/0070504 A1 | 3/2005 | Burgio, Jr. et al. |

FOREIGN PATENT DOCUMENTS

| | | |
|---|---|---|
| CA | 2149052 | 3/2003 |
| EP | 022 751 | 1/1981 |
| EP | 170 228 | 2/1986 |
| EP | 197 478 | 10/1986 |
| EP | 252 504 | 1/1988 |
| EP | 252 505 | 1/1988 |
| EP | 258 618 | 3/1988 |
| EP | 273 190 | 7/1988 |
| EP | 350 002 | 1/1990 |
| EP | 1 135 140 | 8/2005 |
| GB | 2 153 225 | 8/1985 |
| WO | WO 96/17616 | 6/1996 |
| WO | WO 00/61111 | 10/2000 |
| WO | WO 01/01991 | 1/2001 |
| WO | WO 01/15703 | 3/2001 |
| WO | WO 01/76592 | 10/2001 |
| WO | WO 01/89494 A2 | 11/2001 |
| WO | WO 01/89494 A3 | 11/2001 |
| WO | WO 01/97788 A2 | 12/2001 |
| WO | WO 01/97788 A3 | 12/2001 |
| WO | WO 02/00204 | 1/2002 |
| WO | WO 2004/067063 | 8/2004 |

OTHER PUBLICATIONS

Pharmaceutical Dosage Forms, 2nd Edition, 1989, vol. 1, p. 34.

Giron, D. Thermochimica Acta 248-1-59, Elsevier Science B.V., 1995, pp. 1-59.

Goodman & Gilman, Pharmacological Basis of Therapeutics, Ninth Edition, vol. 1, McGraw-Hill, pp. 47,58.

King, Robert E., Pharmaceutical Preparations and Their Manufacturing, Farmacia Practica de Remington, VII pp. 1912-1913.

Giron, D., Journal of Thermal Analysis and Calorimetry, vol. 64, Budapest-2001, p. 38.

Farmacia Remington, Chapter 76-Preformulation, 17 edition, 1987.

Ringe et al., Rheumatology (Oxford), 42(6):743-9 (2003) (PMID:12730532 Abstract).

Schimmer et al., Clin Ther., 25(1):19-34 (2003) (PMID:12637110 Abstract).

Body et al., Support Care Cancer, 10(5):399-407 (2002) (PMID:12136223 Abstract).

Bergner et al., Nephrol Dial Transplant, 17(7):1281-5 (2002) (PMID:12105253 Abstract).

Body et al., J. Clin. Oncol.,16(12):3890-9 (1998) (PMID:9850035 Abstract).

Quimby et al., J. Org. Chem., 32, pp. 4111-4114 (1967).

RUS, B.J., et al ,J. of Bone and Mineral Res., (2001) 16(10), pp. 1871-1878.

Delmas, P.D. et al, Calcified Tissue Intern (2003) 72(4), p. 332.

Chapurlat, R.D., et al, Expert Opinion on Pharmacotherapy, England (2003) 4(3), pp. 391-396.

Hyldstrup et al., Calcified Tissue Int., 53, pp. 297-300 (1993).

Bauss et al., J. Rheumatol., 29, pp. 990-998 (2002).

Monier-Faugere t al., J. Bone Miner. Res., 14, pp. 1768-2778 (1999).

Mazess, Lunar News, pp. 1 and 23 (1996).

Mazess, Lunar News, pp. 1 and 31 (1996).

Nies, A.S., and Spielberg, S.P. Principles of Therapeutics, In Hardman, J.G., and L.E. Limited (Eds.), Goodman & Gilman's the pharmacological bases of therapeutics, ninth edition, pp. 43-62, New York: McGraw-Hill (1996).

* cited by examiner

METHOD OF TREATMENT USING BISPHOSPHONIC ACID

PRIORITY TO RELATED APPLICATIONS

This application is a Continuation of Ser. No. 10/430,007, filed May 6, 2003, which is now pending.

FIELD OF THE INVENTION

The present invention refers to the use of bisphosphonic acids, especially of (1-hydroxy-3-(N-methyl-N-pentyl)aminopropylidene-1,1-bisphosphonic acid (ibandronic acid) or pharmaceutically acceptable salts thereof for the manufacture of pharmaceutical compositions for the prevention or the treatment of disorders characterized by pathologically increased bone resorption, especially for the prevention and treatment of osteoporosis.

BACKGROUND OF THE INVENTION

Bones serve mainly as a support, and consequently bone is frequently regarded as a simple building material. However, bone is a complicated biomaterial adapted to a wide variety of requirements, stimuli and noxae to which it is exposed. Endoprostheses are available as substitutes for bones and joints. However, endoprostheses, even when biomechanically highly refined, do not have an active effect on the environmental and load factors.

A variety of disorders in humans and mammals involve or are associated with abnormal bone resorption. Such disorders include, but are not limited to, osteoporosis, Paget's disease, periprosthetic bone loss or osteolysis, and hypercalcemia of malignancy and metastatic bone disease. The most common of these disorders is osteoporosis, which in its most frequent manifestation occurs in postmenopausal women. Because osteoporosis, as well as other disorders associated with bone loss, are chronic conditions, it is believed that appropriate therapy will generally require chronic treatment.

Bisphosphonates, i.e. bisphosphonic acids or pharmaceutically acceptable salts thereof, are synthetic analogs of the naturally occurring pyrophosphate. Due to their marked affinity for solid-phase calcium phosphate, bisphosphonates bind strongly to bone mineral. Pharmacologically active bisphosphonates are well known in the art and are potent inhibitors of bone resorption and are therefore useful in the treatment and prevention of diseases involving abnormal bone resorption, especially osteoporosis, Paget's disease, hypercalcemia of malignancy, and metastatic and metabolic bone diseases.

Bisphosphonates as pharmaceutical agents are described for example in EP-A-170,228; EP-A-197,478; EP-A-22, 751; EP-A-252,504; EP-A-252,505; EP-A-258,618; EP-A-350,002; EP-A-273,190; and WO-A-90/00798, each of which are incorporated herein by reference.

Pharmaceutical forms of currently marketed bisphosphonates are oral formulations (tablets or capsules) or solutions for intravenous injection or infusion. They are systemically well tolerated when administered at therapeutic doses. However, bisphosphonates as a class are irritant to skin and mucous membranes and when given orally on a continuous basis may result in digestive tract side effects, e.g., esophageal adverse events or gastrointestinal disturbances. As a consequence, and due to their low oral bioavailability, the oral route of administration has, to date, had to follow inconvenient recommendations of use for the patient.

Bisphosphonates can be classified into two groups with different modes of action. Ibandronate belongs to the more potent nitrogen-containing bisphosphonates[Russell 1999 Russell R G G, Rogers M J. Bisphosphonates: From the laboratory to the clinic and back again. Bone 25(1):97–106 (1999); Rogers M J, Gordon S, Benford H L, Coxon F P, Luckman S P, Monkkonen J, Frith J C. Cellular Molecular mechanisms of action of bisphosphonates. Cancer 88 (12) Suppl:2961–2978 (2000)]. Ibandronate is one of the most potent bisphosphonates currently under clinical development in osteoporosis and metastatic bone diseases. In animal models of bone resorption, ibandronate is 2, 10, 50 and 500 times more potent than risedronate, alendronate, pamidronate, and clodronate respectively[Mühlbauer R. C., F. Bauss, R. Schenk, M. Janner, E. Bosies, K. Strein, and H. Fleisch. BM 21.0955 a potent new bisphosphonate to inhibit bone resorption. J. Bone Miner. Res. 6: 1003–1011 (1991)].

Ibandronate inhibits bone resorption without any impairment of mineralization (Mühlbauer et al Mühlbauer R. C., F. Bauss, R. Schenk, M. Janner, E. Bosies, K. Strein, and H. Fleisch. BM 21.0955 a potent new bisphosphonate to inhibit bone resorption. J. Bone Miner. Res. 6: 1003–1011 (1991).). It has been shown to decrease osteoclastic activity, thus inhibiting bone destruction. At high doses it also reduces the number of osteoclasts (Mühlbauer et al. Mühlbauer R. C., F. Bauss, R. Schenk, M. Janner, E. Bosies, K. Strein, and H. Fleisch. BM 21.0955 a potent new bisphosphonate to inhibit bone resorption. J. Bone Miner. Res. 6: 1003–1011 (1991)).

As described, bisphosphonates are accepted as providing strong efficacy in the management of osteoporosis. However, given the administration restrictions related to low oral bioavailability and potential for gastro-intestinal effects, there is a clear opportunity for regimens which offer improved convenience and flexibility, leading to a higher level of compliance and superior patient management/satisfaction. Intermitted regimens such as, for example, once weekly administration have been described in the art.

SUMMARY OF THE INVENTION

It has now been found that the prevention or the treatment of disorders characterized by pathologically increased bone resorption such as osteoporosis, can be improved by a monthly administration of 50 to 250 mg of a bisphosphonate or pharmaceutical acceptable salt thereof, especially by a monthly administration of ibandronate, i.e., ibandronic acid or a pharmaceutically acceptable salt thereof.

The present invention is thus concerned with the use of a bisphosphonic acid or a pharmaceutical acceptable salt thereof, especially with the use of ibandronic acid or a pharmaceutical acceptable salt thereof, for the preparation of pharmaceutical compositions for the prevention or the treatment of disorders characterized by pathologically increased bone resorption, wherein the medicament comprises about 50 to 250 mg, preferably about 100 to 150 mg, of a bisphosphonic acid or a acceptable salt thereof; and orally administered in a period of one, two or three consecutive days per month.

Monthly oral treatment by administration of at least 120%, especially of 120% to 200%, of the expected efficacious daily dose offers incremental patient benefits with respect to convenience and compliance as well as superior results. Prior to the completion of the ibandronate clinical development program, no bisphosphonate had prospectively demonstrated fracture reduction efficacy with a drug-free interval beyond daily administration. In summary, it is quite unexpected that fracture reduction benefit can be derived from a monthly administration of an oral bisphosphonate with a single or multiple tablet administration scheme.

Accordingly, the present invention relates to the use of bisphosphonic acids or pharmaceutically acceptable salts, especially ibandronic acid or pharmaceutically acceptable salts thereof for the manufacture of a medicament for the prevention or treatment of disorders characterized by pathologically increased bone resorption, e.g. osteoporosis, wherein the medicament comprises at least 120% of the expected efficacious daily dose of a bisphosphonic acids or acceptable salts thereof and is administered on one, two or three consecutive days per month.

More preferably the invention comprises the use of ibandronic acid or pharmaceutically acceptable salts thereof for the manufacture of a medicament for the prevention or the treatment of disorders characterized by pathologically increased bone resorption wherein the medicament
a) comprises about 100 to about 150 mg of ibandronic acid or a pharmaceutically acceptable salt thereof and
b) is orally administered in a period of one, two or three consecutive days per month.

DETAILED DESCRIPTION OF THE PREFERRED EMBODIMENT

The term "bisphosphonic acid" means compounds characterized by two phosphonate groups linked by phosphoether bonds to a central (geminal) carbon atom. Such a P—C—P structure is represented by compound I (see, page 6). The use of a specific nomenclature in referring to the bisphosphonate or bisphosphonates is not meant to limit the scope of the present invention, unless specifically indicated.

The term "pharmaceutically acceptable" as used herein means that the salts or chelating agents are acceptable from a toxicity viewpoint.

The term "pharmaceutically acceptable salt" refers to ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth.

The term "disorders characterized by pathologically increased bone resorption" refers to medically defined conditions with or without identifiable cause (such as post-menopausal osteoporosis, idiopathic juvenile osteoporosis, Klinefelter's syndrome; male osteoporosis; osteoporosis due to nutritional factors; organ transplant related osteoporosis; immobilization associated osteoporosis; inflammatory condition and cortico-steroid induced osteoporosis).

The term "one, two or three consecutive days per month" means administration of one to three dose proportional or non-dose proportional tablets on one, two or three consecutive days of the month, preferably on one day per month. As used herein, the term "month" is used in accordance with the generally accepted meaning as a measure of time amounting to approximately four (4) weeks, approximately 30 days, or approximately 1/12 Of a calendar year.

The term "medicament" refers to a pharmaceutical composition. The term encompasses single or multiple administration schemes.

Preferably, the medicament is administered on one day per month. Preferably, the medicament is administered as a single dose, however, the scope of the present invention includes pharmaceutical compositions administered as multiple sub-doses such as on two consecutive day per month or on three consecutive days per month.

Preferably, the medicament comprises at least 100%, preferably 120% to 200% of the efficacious dose of bisphosphonic acids or pharmaceutically acceptable salts thereof, more preferably of ibandronic acid or pharmaceutically acceptable salts thereof.

The term "efficacious dose" refers to about 50 to about 250 mg, more preferably to about 100 to about 150 mg, of a bisphosphonate or a pharmaceutically acceptable salt thereof, for example, of ibandronic acid or a pharmaceutically acceptable salt thereof. As noted, the efficacious dose may be a single dose or multiple sub-doses. For example, if the efficacious dose is 150 mg, the dose may be one (1) 150 mg dose, two (2) 75 mg sub-doses administered on one day or on two consecutive days, or three (3) 50 mg sub-doses administered on one day or on two or three consecutive days; if the efficacious dose is 100 mg, the dose may include one (1) 100 mg dose, two (2) 50 mg sub-doses administered on one day or two consecutive days, preferably on two consecutive days.

"Bisphosphonic acids and pharmaceutically acceptable salts thereof" as pharmaceutical agents are described for example in U.S. Pat. Nos. 4,509,612; 4,666,895; 4,719,203; 4,777,163; 5,002,937 and 4,971,958 and in European Patent Applications Nos. 252,504 and 252,505, herein incorporated by reference for such description.

Methods for the preparation of bisphosphonic acids and pharmaceutically acceptable salts thereof may be found in, e.g., U.S. Pat. Nos. 3,962,432; 4,054,598; 4,267,108; 4,327,039; 4,407,761; 4,621,077; 4,624,947; 4,746,654; 4,970,335; 5,019,651; 4,761,406; 4,876,248; in J. Org. Chem. 32, 4111 (1967) and European Patent Application 252,504, herein incorporated by reference. The pharmaceutically acceptable salts of bisphosphonic acids may also be employed in the instant invention. Examples of base salts of bisphosphonic acids include ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. Non-toxic, physiologically acceptable salts are preferred. The salts may be prepared by methods known in the art, such as described in European Patent Application 252,504 or in U.S. Pat. No. 4,922,077, incorporated herein by reference.

In this invention, the medicament comprises 100 to 150 mg of a ibandronic acid or a pharmaceutically acceptable salt thereof. The pharmaceutical composition comprises at least 150% of a bisphosphonic acid or a pharmaceutically acceptable salt thereof, and one or more pharmaceutically acceptable excipients thereof. In one embodiment, the bisphosphonic acid is ibandronic acid. Preferably, the medicament is administered as a single dose.

In a preferred embodiment of the present invention, the term "bisphosphonate" of the present invention corresponds to compounds of general formula

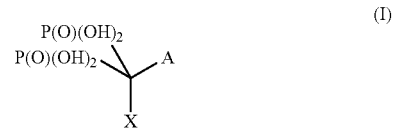

wherein A and X are independently selected from the group consisting of hydrogen, hydroxy, halogen, amino, SH, phenyl, alkyl, mono- or dialkylamino, mono- or dialkylaminoalkyl, alkoxy, thioalkyl, thiophenyl, and aryl or heteroaryl moieties selected from the group consisting of phenyl, pyridyl, furanyl, pyrrolidinyl, imidazolyl, and benzyl, wherein the aryl or heteroaryl moiety is optionally substituted with alkyl.

In the foregoing chemical formula, A can include X, and X include A such that the two moieties can form part of the same cyclic structure.

The foregoing chemical formula is also intended to encompass carbocyclic, aromatic and heteroaromatic structures for the A and/or X substituents, e.g. naphthyl, quinolyl, isoquinolyl, adamantyl, and chlorophenylthio.

Preferred structures are those in which A is selected from the group consisting of hydrogen, hydroxy, and halogen, an X is selected from the group consisting of alkyl, halogen, thiophenyl, thioalkyl and dialkylaminoalkyl.

More preferred structures are those in which A is selected from the group consisting of hydrogen, hydroxy, and Cl and X is selected from the group consisting of alkyl, Cl, chlorophenylthio and dialkylaminoalkyl.

The preferred bisphosphonic acid or pharmaceutically acceptable salt is selected from the group consisting of alendronate, cimadronate, clodronate, tiludronate, etidronate, ibandronate, incadronate, minodronate, neridronate, olpadronate, risedronate, pamidronate, piridronate, zolendronate, EB-1053 or acceptable salts thereof, e.g., ibandronic acid, monosodium salt, monohydrate.

Ibandronic acid (1-hydroxy-3-(N-methyl-N-pentyl)aminopropylidene-1,1-bisphosphonic acid) or physiologically compatible salts thereof are particularly preferred, e.g., ibandronic acid, monosodium salt, monohydrate.

The bisphosphonates and pharmaceutically acceptable salts may be administered alone or in combination with other bone active drugs, either in fixed combinations or separately both physically and in time, including hormones, such as a steroid hormone, e.g., an estrogen; a partial estrogen agonist, or estrogen-gestagen combination; a calcitonin or analogue or derivative thereof, e.g., salmon, eel or human calcitonin parathyroid hormone or analogues thereof, e.g., PTH (1-84), PTH (1-34), PTH (1-36), PTH (1-38), PTH (1-31) or PPTS 893; a SERM (Selective Estrogen Receptor Modulator), e.g., raloxifene, lasofoxifene, TSE-434, FC1271, tibolone, vitamin D or an analog. Such additional bone active drugs may be administered more frequently than the bisphosphonate.

Appropriate pharmaceutical compositions are known in the art and have been described e.g., in U.S. Pat. Nos. 6,143,326 and 6,294,196, herein incorporated by reference.

For the preparation of tablets, coated tablets, drageés or hard gelatine capsules, the compounds of the present invention may be admixed with pharmaceutically inert, inorganic or organic excipients. Examples of suitable excipients for tablets, drageés or hard gelatine capsules include lactose, maize starch or derivatives thereof, talc or stearic acid or salts thereof.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents. Preferably, the pharmaceutical composition is a film coated tablet wherein the tablet core comprises 50 to 200 mg of a bisphosphonic acid or a pharmaceutically acceptable salt thereof as defined above and one or more pharmaceutically acceptable excipients selected from the group consisting of lactose, polyvinylpyrolidone, microcrystalline cellulose, crospovidone, stearic acid, silicon dioxide and the tablet core comprises one or more pharmaceutically acceptable excipients selected from the group consisting of hydroxypropyl methylcellulose, titanium dioxide, talc and polyethylene glycol 6000. These compositions are known in the art and described for example in U.S. Pat. Nos. 6,143,326 and 6,294,196.

Another aspect of the present invention is a method for treating, reducing or preventing disorders characterized by pathologically increased bone resorption comprising to a mammal administration of an effective amount of bisphosphonic acids or acceptable salts thereof. In particular, the invention refers to a method for treating, reducing or preventing disorders characterized by pathologically increased bone resorption comprising oral administration of an effective amount of a bisphosphonic acid or a pharmaceutically acceptable salt thereof, wherein approximately 50 to 250 mg bisphosphonic acid or a pharmaceutically acceptable salt thereof are administered on one, two or three consecutive days per month. As noted above, the effective amount of bisphosphonic acid or pharmaceutically acceptable salt thereof may be administered as a single dose or as multiple sub-doses.

Preferably, in the method comprises administration of about 50 to 250 mg, preferably about 100 to 150 mg, of a bisphosphonate or a pharmaceutically acceptable salt thereof on one, two or three consecutive days per month. While the method includes administration of the dose through multiple sub-dosing, the preferred method provides a single dose. Examples for administration of the dose through multiple sub-dosing are as follows, if the efficacious dose is 150 mg, the dose may be two (2) 75 mg sub-doses administered on one day or on two consecutive days, or three (3) 50 mg sub-doses administered on one day or on two or three consecutive days; if the efficacious dose is 100 mg, the dose may be two (2) 50 mg sub-doses administered on one day or two consecutive days, preferably on two consecutive days. The preferred bisphosphonate is ibandronate or a pharmaceutically acceptable salt thereof, e.g., ibandronic acid, monosodium salt, monohydrate.

Preferably, in the method according to the present invention, the bisphosphonic acid is selected from the group consisting of alendronate, cimadronate, clodronate, tiludronate, etidronate, ibandronate, incadronate, minodronate, neridronate, olpadronate, risedronate, pamidronate, piridronate, zolendronate, EB-1053 or pharmaceutical acceptable salts thereof. More preferably, the bisphosphonic acid is ibandronate or a pharmaceutically acceptable salt thereof, e.g. ibandronic acid, monosodium salt, monohydrate.

The invention will now be explained with reference to exemplified embodiments.

EXAMPLES

Example 1

Pharmaceutical Composition

The Example shows the composition of a 50 mg tablet. The composition and preparation of these tablets is known in the art and described for example in U.S. Pat. Nos. 6,143,326 and 6,294,196.

Other compositions may be prepared by adjusting the ingredients according to the amount of bisphosphonate, e.g. ibandronic acid, monosodium salt, monohydrate.

| 50 mg film-coated tablet | |
|---|---|
| Components | mg per tablet |
| Tablet core: | |
| Ibandronic acid, monosodium salt, monohydrate | 56.250 |
| Lactose monohydrate | 92.750 |
| Povidone K 25 | 5.000 |
| Microcrystalline cellulose | 30.000 |
| Crospovidone | 10.000 |
| Purified stearic acid | 4.000 |
| Colloidal silicon dioxide | 2.000 |
| Tablet coat: | |
| Hydroxypropyl methylcellulose | 5.1425 |
| Titanium dioxide | 2.4650 |
| Talc | 0.8925 |
| Polyethylene glycol 6,000 | 1.5000 |
| Final weight: | 210.000 |

What is claimed is:

1. A method for treating or inhibiting osteoporosis comprising commencing treatment by orally administering to a subject in need of such treatment, a first dose, on a single day, of a pharmaceutical composition comprising from about 100 mg to about 150 mg of bisphosphonic acid or an amount of a pharmaceutically acceptable salt thereof that is equivalent to about 100 mg to about 150 mg of said bisphosphonic acid and continuing said treatment by orally administering, once monthly on a single day, a pharmaceutical composition comprising from about 100 mg to about 150 mg of bisphosphonic acid or an amount of a pharmaceutically acceptable salt thereof that is eguivalent to from about 100 mg to about 150 mg of bisphosphonic acid.

2. The method according to claim 1, wherein the pharmaceutical composition comprises about 100 mg of bisphosphonic acid or an amount of a pharmaceutically acceptable salt thereof that is equivalent to about 100 mg of bisphosphonic acid.

3. The method according to claim 1, wherein the pharmaceutical composition comprises about 150 mg of bisphosphonic acid or an amount of a pharmaceutically acceptable salt thereof that is equivalent to about 150 mg of bisphosphonic acid.

4. The method of claim 1, wherein the pharmaceutical composition comprises 100 mg of bisphosphonic acid or an amount of a pharmaceutically acceptable salt thereof that is equivalent to 100 mg of bisphosphonic acid.

5. The method of claim 1 wherein the pharmaceutical composition comprises 150 mg of bisphosphonic acid or an amount of a pharmaceutically acceptable salt thereof that is equivalent to 150 mg of bisphosphonic acid.

6. The method of claim 1 wherein said bisphosphonic acid is risedronic acid or a pharmaceutically acceptable salt thereof.

7. The method of claim 2 wherein said bisphosphonic acid is risedronic acid or a pharmaceutically acceptable salt thereof.

8. The method of claim 3 wherein said bisphosphonic acid is risedronic acid or a pharmaceutically acceptable salt thereof.

9. The method of claim 5 wherein said bisphosphonic acid is risedronic acid or a pharmaceutically acceptable salt thereof.

10. The method of claim 1 wherein said pharmaceutical composition is a solid pharmaceutical composition.

11. The method of claim 3 wherein said pharmaceutical composition is a solid pharmaceutical composition.

12. The method of claim 5 wherein said pharmaceutical composition is a solid pharmaceutical composition.

13. The method of claim 6 wherein said pharmaceutical composition is a solid pharmaceutical composition.

14. The method of claim 8 wherein said pharmaceutical composition is a solid pharmaceutical composition.

15. The method of claim 9 wherein said pharmaceutical composition is a solid pharmaceutical composition.

16. A method for treating or inhibiting osteoporosis consisting of orally administering to a subject in need of such treatment, once monthly, a pharmaceutical composition comprising from about 100 mg to about 150 mg of bisphosphonic acid or an amount of a pharmaceutically acceptable salt thereof that is equivalent to about 100mg to about 150mg of said bisphosphonic acid.

17. The method according to claim 16, wherein the pharmaceutical composition comprises about 100 mg of bisphosphonic acid or an amount of a pharmaceutically acceptable salt thereof that is equivalent to about 100 mg of bisphosphonic acid.

18. The method according to claim 16, wherein the pharmaceutical composition comprises about 150 mg of bisphosphonic acid or an amount of a pharmaceutically acceptable salt thereof that is equivalent to about 150 mg of bisphosphonic acid.

19. The method of claim 16 wherein the pharmaceutical composition comprises 100 mg of bisphosphonic acid or an amount of a pharmaceutically acceptable salt thereof that is equivalent to 100 mg of bisphosphonic acid.

20. The method of claim 16 wherein the pharmaceutical composition comprises 150 mg of bisphosphonic acid or an amount of a pharmaceutically acceptable salt thereof that is equivalent to 150 mg of bisphosphonic acid.

21. The method of claim 16 wherein said bisphosphonic acid is risedronic acid or a pharmaceutically acceptable salt thereof.

22. The method of claim 17 wherein said bisphosphonic acid is risedronic acid or a pharmaceutically acceptable salt thereof.

23. The method of claim 18 wherein said bisphosphonic acid is risedronic acid or a pharmaceutically acceptable salt thereof.

24. The method of claim 20 wherein said bisphosphonic acid is risedronic acid or a pharmaceutically acceptable salt thereof.

25. The method of claim 16 wherein said pharmaceutical composition is a solid pharmaceutical composition.

26. The method of claim 18 wherein said pharmaceutical composition is a solid pharmaceutical composition.

27. The method of claim 20 wherein said pharmaceutical composition is a solid pharmaceutical composition.

28. The method of claim 16 wherein said pharmaceutical composition is a solid pharmaceutical composition.

29. The method of claim 18 wherein said pharmaceutical composition is a solid pharmaceutical composition.

30. The method of claim 20 wherein said pharmaceutical composition is a solid pharmaceutical composition. once monthly on a single day, a pharmaceutical composition comprising from about 100 mg to about 150 mg of bisphosphonic acid acceptable salt thereof that is eguivalent to from about 100 mg to about 150 mg of bisphosphonic acid.

* * * * *

UNITED STATES PATENT AND TRADEMARK OFFICE
CERTIFICATE OF CORRECTION

PATENT NO. : 7,192,938 B2  Page 1 of 1
APPLICATION NO. : 10/998849
DATED : March 20, 2007
INVENTOR(S) : Bauss et al.

It is certified that error appears in the above-identified patent and that said Letters Patent is hereby corrected as shown below:

Column 8, Claim 28, line 54, delete "16" and insert --21-- therefor.

Column 8, Claim 29, line 56, delete "18" and insert --23-- therefor.

Column 8, Claim 30, line 58, delete "20" and insert --24-- therefor.

Column 8, Claim 30, lines 61-65, delete "once monthly on a single day, a pharmaceutical composition comprising from about 100 mg to about 150 mg of bisphosphonic acid acceptable salt thereof that is eguivalent to from about 100 mg to about 150 mg of bisphosphonic acid."

Signed and Sealed this

Nineteenth Day of June, 2007

JON W. DUDAS
*Director of the United States Patent and Trademark Office*